(12) United States Patent
Kim et al.

(10) Patent No.: US 7,459,572 B2
(45) Date of Patent: Dec. 2, 2008

(54) PROCESS FOR THE PREPARATION OF GLYCIDYL DERIVATIVES

(75) Inventors: Seong-Jin Kim, Daejeon (KR); Ho-Seong Lee, Daejeon (KR); Jin-Won Yun, Daejeon (KR); Ho-Cheol Kim, Daejeon (KR)

(73) Assignee: RSTECH Corporation, Daejeon (KR)

( * ) Notice: Subject to any disclaimer, the term of this patent is extended or adjusted under 35 U.S.C. 154(b) by 0 days.

(21) Appl. No.: 11/660,491

(22) PCT Filed: Aug. 19, 2004

(86) PCT No.: PCT/KR2004/002093

§ 371 (c)(1),
(2), (4) Date: Feb. 16, 2007

(87) PCT Pub. No.: WO2006/019202

PCT Pub. Date: Feb. 23, 2006

(65) Prior Publication Data

US 2007/0265458 A1 Nov. 15, 2007

(51) Int. Cl.
*C07D 301/26* (2006.01)

(52) U.S. Cl. ...................... 549/515; 549/514
(58) Field of Classification Search ............... 549/518, 549/555, 521, 515, 514, 516
See application file for complete search history.

(56) References Cited

U.S. PATENT DOCUMENTS 4,946,974 A 8/1990 Sharpless et al.
5,965,753 A 10/1999 Masaki et al.

FOREIGN PATENT DOCUMENTS

EP 0 884 313 12/1998

*Primary Examiner*—B. Dentz
*Assistant Examiner*—David E Gallis
(74) *Attorney, Agent, or Firm*—Hoffmann & Baron, LLP

(57) ABSTRACT

There is provided a process for preparing a glycidyl derivative from 3-chloro-1,2-propanediol, comprising i) adding a phosphate salt to a solution into which 3-chloro-1,2-propanediol is dissolved into a solvent to produce glycidol, and ii) adding to the solution of step i) a base capable of releasing a glycidyl group from the glycidol and a substrate susceptible to nucleophilic attack to produce the desired glycidyl derivative by nucleophilic attack of the glycidyl group to the substrate.

12 Claims, No Drawings

PROCESS FOR THE PREPARATION OF GLYCIDYL DERIVATIVES

TECHNICAL FIELD

The present invention relates to a process for the preparation of glycidyl derivatives. More specifically, the present invention relates to a process for the preparation of glycidyl derivatives from 3-chloro-1,2-propanediol.

BACKGROUND ART

Glycidyl derivatives are essential intermediates used for the preparation of medicines, agricultural articles, bio-products and fine-chemicals [*Chemical Reviews*, Vol. 91, 437 (1991)]. Generally, the glycidyl derivatives are prepared by derivatizing glycidol in a presence of a base and a solvent. The yield and optical purity of the glycidyl derivatives are largely dependent upon reaction conditions.

U.S. Pat. Nos. 4,946,974 and 5,252,759, and Japanese unexamined patent publication No. 6-179663 disclose a process for producing glycidyl derivatives, comprising reacting glycidol with a substrate in a presence of a tertiary amine, in an organic solvent or in a two phase solvent consisting of an organic solvent and water. Due to the instability of the glycidol, the process produces various side products. In addition, the reaction rate is so slow that the process is not economical.

In order to overcome the disadvantages, Japanese unexamined patent publication No. 7-165743 discloses a process for the preparation of glycidyl derivatives, comprising treating 3-chloro-1,2-propanediol with an alkali metal carbonate in an organic solvent and without isolation of the resulting glycidyl, subjecting it to reaction with p-toluenesulfonyl chloride, a tertiary amine and 4-(dimethylamino)pyridine to produce glycidyl tosylate. As indicated in U.S. Pat. No. 5,965,753 filed by the same applicant, however, the process suffers from disadvantages that the reaction rate is low and various side products are produced, which deteriorates chemical purities and optical purities of the desired products.

As an improvement of the process of the Japanese unexamined patent publication No. 7-165743, U.S. Pat. No. 5,965,753 discloses a process for the preparation of a glycidylsulfonate derivative in one reaction vessel which is characterized in that reacting 3-chloro-1,2-propanediol in an aqueous solvent in a presence of a hydroxide salt or a carbonate salt, and without isolating the resulting glycidol, subjecting it to reaction with a sulfonyl halide in a two phase solvent consisting of an organic solvent and water in the presence of at least one inorganic base selected from the group consisting of a hydroxide salt and a carbonate salt, and a tertiary amine or a pyridine derivative. However, the process has very narrow applicability, for example, to the preparation of a chiral glycidyl sulfonate from sulfonyl chloride which is stable in water. The process can not be applicable to acid halides (or acyl halide) or acid anhydrides which are sensitive to the presence of water. Furthermore, as suggested in German patent No. 1,226,554 and U.S. Pat. No. 2,248,635, the carbonate salt is generally used in an organic solvent, and a hydroxide salt in an aqueous solvent.

DISCLOSURE OF INVENTION

Technical Problem

As shown in the above documents, the prior art fails to disclose or suggest usefulness of a phosphate salt in the preparation of glycidyl derivatives from 3-chloro-1,2-propanediol in one reaction vessel. The phosphate salt has a stronger basicity than the carbonate salt, and has a fine particle size. For these reasons, the phosphate salt is expected to accelerate the reaction rate in an organic solvent system.

An object of the present invention is to provide a process for producing glycidyl derivatives from 3-chloro-1,2-propanediol in one reaction vessel in high purity, with high yield and in an accelerated reaction rate.

Another object of the present invention is to provide a process for producing glycidyl derivatives from 3-chloro-1,2-propanediol which is applicable to various substrates including water-sensitive substrates.

Further another object of the present invention is to provide a process which produces glycidyl derivatives in high optical purity.

Technical Solution

According to preferred embodiment of the present invention, there is provided a process for preparing a glycidyl derivative from 3-chloro-1,2-propanediol, comprising i) adding a phosphate salt to a solution into which 3-chloro-1,2-propanediol is dissolved into a solvent to produce glycidol, and ii) adding to the solution of step i) a base capable of releasing a glycidyl group from the glycidol and a substrate susceptible to nucleophilic attack to produce the desired glycidyl derivative by nucleophilic attack of the glycidyl group to the substrate.

According to another preferred embodiment of the present invention, there is provided a process for preparing a glycidyl derivative from 3-chloro-1,2-propanediol in which both conversion of 3-chloro-1,2-propanediol into glycidol of the step i) and nucleophilic attack of the glycidyl group to the substrate of the step ii) are performed in one reaction vessel.

According to another preferred embodiment of the present invention, there is provided a process for preparing a glycidyl derivative from 3-chloro-1,2-propanediol in which both conversion of 3-chloro-1,2-propanediol into glycidol of the step i) and nucleophilic attack of the glycidyl group to the substrate of the step ii) are performed in one reaction vessel and in an anhydrous solvent system consisting essentially of an organic solvent.

According to another preferred embodiment of the present invention, there is provided a process for preparing a glycidyl derivative from 3-chloro-1,2-propanediol in which the nucleophilic attack of the glycidyl group to the substrate is performed without any isolation of the glycidol produced in the step i).

According to further another preferred embodiment of the present invention, there is provided a process for preparing a glycidyl derivative from 3-chloro-1,2-propanediol in which chirality of 3-chloro-1,2-propanediol is retained.

Advantageous Effects

As stated in the above, Japanese unexamined patent publication No. 7-165743 produces glycidyl derivatives in a one-phase organic solvent system, but the yield and the purity of the final product are very poor. Further, it requires complicated purification processes. To the contrary, the process according to the present invention provides glycidyl derivatives in high yield, with high chemical purity and high optical purity. The reaction rate is also accelerated. Various glycidyl derivatives are prepared including a chiral glycidyl alkanoate as well as a chiral glycidyl sulfonate.

MODE FOR INVENTION

The present invention relates to a process for preparing a glycidyl derivative from 3-chloro-1,2-propanediol, comprising i) adding a phosphate salt to a solution into which 3-chloro-1,2-propanediol is dissolved into a solvent to produce glycidol, and ii) adding to the solution of step i) a base capable of releasing a glycidyl group from the glycidol and a substrate susceptible to nucleophilic attack to produce the desired glycidyl derivative by nucleophilic attack of the glycidyl group to the substrate.

The process according to the present invention can be summarized in a reaction scheme I:

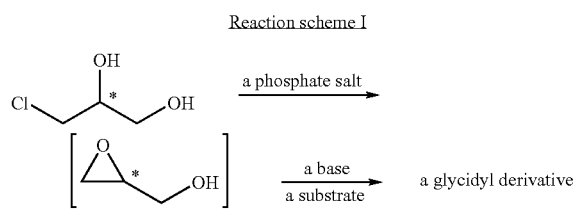

Reaction scheme I wherein, *represents a chiral center.

As shown in the reaction scheme 1, the starting material 3-chloro-1,2-propanediol is firstly converted to glycidol by the treatment of a phosphate salt, which is one of features of the present invention. The resulting glycidol reacts with a substrate susceptible to nucleophilic attack with aid of a base to produce the desired glycidyl derivative. Herein, the glycidol is preferably not isolated from a reaction vessel, but participates in situ nucleophilic substitution. That is, both the conversion of 3-chloro-1,2-propanediol to glycidol and the nucleophilic attack of the resulting glycidol to a substrate are performed in one reaction vessel, without any isolation of the resulting glycidol.

The phosphate salt has a stronger basicity than a carbonate salt, and has a fine particle size. As a result thereof, the reactivity of the phosphate salt in an organic solvent is superior to the carbonate salt, which accelerates the reaction rate of the process. In an industrial case in which the carbonate salt is used in an organic solvent, the reaction rate was found to be slower as the reaction scale was larger. Such a tendency was found to be reinforced as the particle size of the carbonate salt was larger. Therefore, the carbonate salt is believed to have a limitation to an industrial applicability. To the contrary, the phosphate salt having high basicity and fine particle size was found to sufficiently accelerate the production of the glycidol used as an intermediate, and be independent of the reaction scale. Fast production of the glycidol reduced the probability of side reactions as well as the probability of racemization. Thus, the use of the phosphate salt instead of the carbonate salt increases both the yield and the optical purity of the desired glycidyl derivative.

As a phosphate salt, monobasic, dibasic or tribasic form of a phosphate salt can be used. As a metal ion which forms a salt with phosphate, an alkali metal phosphate or an alkali earth metal can be mentioned, but are not limited thereto. According to preferred embodiment of the present invention, potassium phosphate tribasic ($K_3PO_4$) was used as a phosphate salt and gave a satisfactory result. The phosphate salt is used in an amount of 1□2 molar ratio relative to 3-chloro-1,2-propanediol.

Preferably, both the conversion of 3-chloro-1,2-propanediol to glycidol and the nucleophilic attack of the resulting glycidol to a substrate are performed in an anhydrous solvent system consisting essentially of an organic solvent. This provides another advantage that the process according to the present invention can be applicable to a substrate which is sensitive to the presence of water, such as acyl halide or acid anhydride. As an anhydrous solvent, various organic solvents such as aliphatic hydrocarbon unsubstituted or substituted with at least one heteroatom selected from the group consisting of oxygen, nitrogen and halogen, or aromatic hydrocarbon unsubstituted or substituted with at least one heteroatom selected from the group consisting of oxygen, nitrogen and halogen can be mentioned. Specifically, haloalkane such as methylene chloride and chloroform, ether such as tetrahydrofuran, or benzene and toluene can be used as an organic solvent.

With regard to a base which attracts hydrogen of glycidol and releases the glycidyl group that act as a nucleophile, please refer to the above mentioned U.S. Pat. No. 5,965,753. Specifically, an organic base such as tertiary amines or pyridine derivatives can be mentioned as a base. The tertiary amines include an aliphatic amine and an aromatic amine. A trialkyl amine such as trimethylamine, triethylamine or diisopropylethylamine is preferably used as a base. More preferably, a combination of the tertiary amine and a catalytic amount of the pyridine derivative such as 4-(dimethylamino)pyridine is used as a base. The base is used in an amount of 1□2 molar ratio relative to 3-chloro-1,2-propanediol.

The glycidol reacts with a substrate with aid of a base to produce the targeted glycidyl derivative. As used herein, the term "substrate" is defined as the compound on which substitution takes place. In the case of nucleophilic substitution, the substrate is characterized by the presence of a leaving group: the group that becomes displaced with a nucleophile, and departs from the compound. The substrate to be used is not particularly limited. An alkyl halide, an acyl halide, an acid anhydride and a sulfonyl halide can be mentioned as a substrate to be used. An acyl halide or an acid anhydride is preferable. Of the acyl halide, acyl chloride is preferable. The substrate is added to the solution in an amount of 1□2 molar ratio, preferably 1□1.2 molar ratio, relative to 3-chloro-1,2-propanediol.

In the process according to the present invention, the preparation of glycidol is carried out at a temperature of 10□100° C., preferably 20□40° C. The preparation of the glycidyl derivative is performed at a temperature of 0□40° C., preferably 0□25° C.

The resulting reaction mixture of the glycidol derivative produced by derivatization of glycidol in one reaction vessel is subjected to an ordinary work up procedure. Various work-up methods can be adopted depending on the physical property of the glycidol derivative, which are well known in the art. For example, fractional distillation or recrystallization can be performed in order to isolate the desired glycidyl derivative. According to specific examples of the present invention, the glycidol derivative was produced in high yield and few impurities were produced, which facilitate isolation of the glycidol derivative from the reaction mixture. The produced glycidol derivative was found to retain chirality of the starting material, 3-chloro-1,2-propanediol.

According to the preferred embodiment of the present invention, the glycidyl derivative has a formula I:

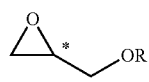

Formula I wherein, R represents a substituent and * represents a chiral center.

The substituent R of the glycidyl derivative includes an alkyl group, an acyl group and a sulfonyl group.

The present invention will be more fully illustrated referring to the following Examples. However, it should be understood that these Examples are suggested only for illustration and should not be construed to limit the scope of the present invention. Numerous modifications could be made without departing from the scope and the spirit of the invention.

EXAMPLES

Example 1

Preparation of (R)-glycidyl gutyrate

To 1.2 L of a methylene chloride solution of (S)-3-chloro-1,2-propanediol (200g, 99.5% ee) was added 519g of potassium phosphate tribasic, and then the obtained solution was refluxed, under stirring, for 3 hours. The resulting solution was cooled to 0° C., and 220g of triethylamine, 4g of 4-(dimethylamino)pyridine, and 315g of butanoic acid anhydride were dropwisely added to the solution. After additional stirring for 1 hour at a room temperature, the reaction mixture was successively washed with 2.2 L of 5% aqueous potassium carbonate solution, 2 L of 1N aqueous hydrogen chloride solution, and 1 L of water. The organic layer was dried with 50g of anhydrous sodium sulfate and filtrated. The methylene chloride was evaporated under reduced pressure. Fractional distillation (90° C./19 mmHg) of the resulting residue gave 242g of the targeted compound:
Yield: 92.7%
Chemical purity: 99.4%
Optical purity (GC): 99.5% ee Example 2

Preparation of (S)-Glycidyl Butyrate

To 1.2 L of a methylene chloride solution of (R)-3-chloro-1,2-propanediol (200g, 99.5% ee) was added 519g of potassium phosphate tribasic, and then the obtained solution was refluxed, under stirring, for 3 hours. The resulting solution was cooled to 0° C., and 220g of triethylamine and 212g of butyryl chloride were dropwisely added to the solution. After additional stirring for 1 hour at a room temperature, the reaction mixture was successively washed with 2.2 L of 5% aqueous potassium carbonate solution, 2 L of 1N aqueous hydrogen chloride solution, and 1 L of water. The organic layer was dried with 50 g of anhydrous sodium sulfate and filtrated. The methylene chloride was evaporated under reduced pressure. Fractional distillation (90° C./19 mmHg) of the resulting residue gave 243g of the targeted compound:
Yield: 93.1%
Chemical purity: 99.4%
Optical purity (GC): 99.4% ee Example 3

Preparation of (S)-glycidyl tosylate

To 1.2 L of a methylene chloride solution of (R)-3-chloro-1,2-propanediol (200g, 99.5% ee) was added 499g of potassium phosphate tribasic, and then the obtained solution was refluxed, under stirring, for 3 hours. The resulting solution was cooled to 0° C., and 201 g of triethylamine, 4g of 4-(dimethylamino)pyridine, and tosyl chloride (69 g×5) was added to the solution. After additional stirring for 1 hour at a room temperature, the reaction mixture was successively washed with 2.2 L of 5% aqueous potassium carbonate solution, 2 L of 1N aqueous hydrogen chloride solution, and 1 L of water. The organic layer was dried with 50g of anhydrous sodium sulfate and filtrated. Evaporation of the methylene chloride under reduced pressure gave a crude product (chemical purity: 99.3%, optical purity 99.5% ee). After addition of hexane to the resulting residue, the obtained solid product was filtrated to give 337g of the targeted product:
Yield: 81.5%
Chemical purity: 99.8%
Optical purity (GC): 99.5% ee
Melting point: 47~49° C.

Example 4

Preparation of (R)-glycidyl tosylate (R)-glycidyl tosylate was prepared in the same manner as described in Example 3 except that (S)-3-chloro-1,2-propanediol (99.4% ee) was used instead of the (R)-3-chloro-1,2-propanediol:
Yield: 340g, 82.3%
Chemical purity: 99.8%
Optical purity: 99.4%
Melting point: 47~49° C.

Example 5

Preparation of (S)-glycidyl-3-nitrobenzenesulfonate (S)-glycidyl-3-nitrobenzenesulfonate was prepared in the same manner as described in Example 3 except that 401g of 3-nitrobenzenesulfonyl chloride was used instead of the tosyl chloride, and that the residue was recystallized from hexane/ethyl acetate=1:1 (V/V):
Yield: 378 g, 80.5%
Chemical purity: 99.2%
Optical purity (GC): 99.5% ee
Melting point: 64~66° C.

Example 6

Preparation of (R)-glycidyl methacrylate (R)-glycidyl methacrylate was prepared in the same manner as described in Example 1 except that 307g of methacrylic acid anhydride was used instead of the butanoic acid anhydride, and that the fractional distillation was carried out at 80~85° C., 19 mmHg:
Yield: 223 g, 86.5%
Chemical purity: 98.5%
Optical purity (GC): 99.5% ee

Example 7

Preparation of (S)-glycidol

To 1.2 L of methylene chloride, 200g of (R)-3-chloro-1,2-propanediol (99.5% ee) and 419g of potassium phosphate tribasic was added. The obtained solution was refluxed under stirring for 3 hours. The resulting solution was cooled to a room temperature and filtrated. The methylene chloride was evaporated under reduced pressure. Fractional distillation (66° C./19 mmHg) of the resulting residue gave 122 g of the targeted compound:
 Yield: 91.0%
 Chemical purity: 99.0%
 Optical purity (GC): 99.5% ee

Comparative Example 1

Preparation of (R)-glycidyl butyrate

To 1.2 L of a methylene chloride solution of (S)-3-chloro-1,2-propanediol (200g, 99.5% ee) was added 338g of potassium carbonate, and then the obtained solution was refluxed, under stirring, for 25 hours. The resulting solution was cooled to 0° C., and 220g of triethylamine, 4g of 4-(dimethylamino) pyridine, and 315 g of butanoic acid anhydride were dropwisely added to the solution. After additional stirring for 1 hour at a room temperature, the reaction mixture was successively washed with 2.2 L of 5% aqueous potassium carbonate solution, 2 L of 1N aqueous hydrogen chloride solution, and 1 L of water. The organic layer was dried with 50 g of anhydrous sodium sulfate and filtrated. The methylene chloride was evaporated under reduced pressure. Fractional distillation (90° C./19mmHg) of the resulting residue gave 170g of the targeted compound:
 Yield: 65.0%
 Chemical purity: 97.4%
 Optical purity (GC): 98.1% ee As shown in the above, the process according to the present invention provides glycidyl derivatives in high yield, with high chemical purity and high optical purity, compared to the conventional one in which the carbonate salt was used. In addition, the reaction rate of the phosphate salt is even faster than that of the carbonate salt. Therefore, the process according to the present invention is an industrially advantageous one. Furthermore, the process according to the present invention can be applicable to the preparation of various glycidyl derivatives including a chiral glycidyl alkanoate as well as a chiral glycidyl sulfonate.

The invention claimed is:

1. A process for preparing a glycidyl derivative from 3-chloro-1,2-propanediol, comprising the steps of:
 (i) adding a tribasic alkali phosphate salt to a solution into which 3-chloro-1,2-propanediol is dissolved into a solvent to produce glycidol; and,
 (ii) adding to the solution of step (i) a base capable of releasing a glycidyl group from the glycidol and a substrate susceptible to nucleophilic attack selected from the group consisting of an acyl halide, an acid anhydride and a sulfonyl halide to produce the desired glycidyl derivative by nucleophilic attack of the glycidyl group to the substrate.

2. The process as set forth in claim 1, wherein both conversion of 3-chloro-1,2-propanediol into glycidol of the step (i) and nucleophilic attack of the glycidyl group to the substrate of the step (ii) are performed in one reaction vessel.

3. The process as set forth in claim 1, wherein both conversion of 3-chloro-1,2-propanediol into glycidol of the step (i) and nucleophilic attack of the glycidyl group to the substrate of the step (ii) are performed in one reaction vessel and in an anhydrous solvent system consisting essentially of an organic solvent.

4. The process as set forth in claim 1, wherein the nucleophilic attack of the glycidyl group to the substrate is performed without any isolation of the glycidol produced in the step (i).

5. The process as set forth in claim 1, wherein the substrate is selected from the group consisting of an acyl halide and an acid anhydride.

6. The process as set forth in claim 1, wherein the phosphate salt is a tribasic potassium phosphate salt.

7. The process as set forth in claim 1, wherein the organic solvent is haloalkane.

8. The process as set forth in claim 1, wherein the base is an organic base.

9. The process as set forth in claim 1, wherein the 3-chloro-1,2-propanediol has chirality, and the chirality is retained in the glycidyl derivative.

10. The process as set forth in claim 1, further comprising isolating the desired glycidyl derivative by fractional distillation or recrystallization.

11. A method for preparing glycidol which comprises treating 3-chloro-1,2-propanediol with a basic salt, characterized in that the basic salt is a tribasic alkali phosphate salt.

12. The method as set forth in claim 11, wherein the tribasic alkali phosphate salt is a tribasic potassium phosphate salt.

* * * * *

UNITED STATES PATENT AND TRADEMARK OFFICE
CERTIFICATE OF CORRECTION

PATENT NO.         : 7,459,572 B2
APPLICATION NO. : 11/660491
DATED              : December 2, 2008
INVENTOR(S)        : Kim et al.

It is certified that error appears in the above-identified patent and that said Letters Patent is hereby corrected as shown below:

Column 3, line 66, replace "amount of 1□2 molar ratio" with --amount of 1-2 molar ratio--;

Column 4, line 32, replace "amount of 1□2 molar ratio" with --amount of 1-2 molar ratio--;

Column 4, line 46, replace "amount of 1□2 molar ratio" with --amount of 1-2 molar ratio--;

Column 4, line 47, replace "preferably 1□1.2 molar ratio" with --preferably 1-1.2 molar ratio--;

Column 4, line 50, replace "temperature of 10□100°C.," with --temperature of 10-100°C.,--;

Column 4, line 51, replace "preferably 20□40°C." with --preferably 20-40°C.--;

Column 4, line 52, replace "temperature of 0□40°C., preferably" with --temperature of 0-40°C., preferably--;

Column 4, line 53, replace "preferably 0□25°C." with --preferably 0-25°C.--;

Column 6, line 25, replace "Melting point: 47□49°C." with --Melting point: 47-49°C.--;

Column 6, line 39, replace "Melting point: 47□49°C." with --Melting point: 47-49°C.--;

Column 6, line 48, replace "residue was recystallized" with --residue was recrystallized--;

Column 6, line 54, replace "Melting point: 64□66°C." with --Melting point: 64-66°C.--;

UNITED STATES PATENT AND TRADEMARK OFFICE
CERTIFICATE OF CORRECTION

PATENT NO. : 7,459,572 B2
APPLICATION NO. : 11/660491
DATED : December 2, 2008
INVENTOR(S) : Kim et al.

It is certified that error appears in the above-identified patent and that said Letters Patent is hereby corrected as shown below:

Column 6, line 63, replace "carried out at 80□85°C.," with --carried out at 80-85°C.,--.

Signed and Sealed this

Nineteenth Day of May, 2009

JOHN DOLL
*Acting Director of the United States Patent and Trademark Office*